United States Patent [19]

Donahoe

[11] Patent Number: 5,010,055
[45] Date of Patent: Apr. 23, 1991

[54] USE OF EGF TO REVERSE THE CONTRACEPTIVE ACTIVITY OF MIS

[75] Inventor: Patricia K. Donahoe, Weston, Mass.

[73] Assignee: The General Hospital Corporation, Boston, Mass.

[21] Appl. No.: 205,239

[22] PCT Filed: Jun. 24, 1987

[86] PCT No.: PCT/US87/01514
§ 371 Date: Apr. 25, 1988
§ 102(e) Date: Apr. 25, 1988

[87] PCT Pub. No.: WO88/00054
PCT Pub. Date: Jan. 14, 1988

Related U.S. Application Data

[63] Continuation-in-part of Ser. No. 877,735, Jun. 24, 1986, Pat. No. 4,753,794.

[51] Int. Cl.[5] ............... A61K 37/36; A61K 37/38
[52] U.S. Cl. .................................... 514/8; 514/12
[58] Field of Search ......................... 514/8, 12

[56] References Cited

U.S. PATENT DOCUMENTS 4,753,794  6/1988  Donahoe et al. .............. 514/8
4,792,601  12/1988  Donahoe et al. ............ 530/387

OTHER PUBLICATIONS

Dekel et al., Endocrinology, vol. 116: 406–409, 1985.
Takahashi et al., Mol. Cell. Endocrinology, Oct. 1986, 47(8), pp. 225–234 (Abstract).

Primary Examiner—Howard E. Schain
Assistant Examiner—Choon P. Koh
Attorney, Agent, or Firm—Sterne, Kessler, Goldstein & Fox

[57] ABSTRACT

The invention discloses a novel use of Mullerian Inhibiting Substance (MIS) as a contraceptive agent. MIS has been found to reversably inhibit the maturation of oocytes in vitro. Additionally, the invention provides a means for restoring the fertility of females who are infertile due to abnormal production of MIS.

4 Claims, 10 Drawing Sheets

USE OF EGF TO REVERSE THE CONTRACEPTIVE ACTIVITY OF MIS

CROSS-REFERENCE TO RELATED APPLICATIONS

This application is a continuation-in-part of U.S. patent application Ser. No. 06/877,735 (filed June 24, 1986), which issued as U.S. Pat. No. 4,753,794 on June 28, 1988.

FIELD OF THE INVENTION

The present invention relates to Mullerian Inhibiting Substance, and its use as a contraceptive agent.

BACKGROUND ART

I. Mullerian Inhibiting Substance

Mullerian Inhibiting Substance (MIS) is a 140,000 dalton glycoprotein responsible for the regression of the Mullerian duct in a male embryo (Jost, A., *Comptes Rend. Soc. Biol.*, 140:463-464 (1946); Jost, A., *Comptes Rend. Soc. Biol.*, 141:135-136 (1947); Balanchard, M. G., et al., *Ped. Res.*, 8:968-971 (1974); Donahoe, P.K., et al., *Biol. Repro.*, 15:329-334 (1976); Donahoe, P. K., et al., *J. Ped. Surg.*, 12:323-330 (1977); Donahoe, P. K., et al., *Biol. Repro.*, 16:238-243 (1977)).

Mullerian Inhibiting Substance has been found to be a glycoprotein hormone. The substance is produced by fetal and neonatal Sertoli cells of the testes. MIS has been partially purified and found to be a dimeric glycoprotein of 72,000 and 74,000 daltons (Budzik, G. P., et al., In: Lash, J. W., Saxen, L., (Eds.), *Developmental Mechanisms: Normal and Abnormal.* N.Y., Alan R. Liss, pp. 207-223 (1985)). The purification of MIS is described in Donahoe, P. K., et al. (U.S. Pat. No. 4,510,131).

Monoclonal antibodies to MIS have been developed and found to be useful in the purification and preparation of MIS (Shima, H., et al., *Hybridoma* 3:201-214 (1984); Donahoe, P. K., et al., U.S. Pat. No. 4,487,833 Necklaws, E. C., et al., *Endocrinology* 118:791-796 (1986). Using these monoclonal antibodies, a radioimmunoassay has been developed to detect MIS (Hayashi, M., et al., *J. Histochem. Cytochem.*, 32:649-654 (1984)). This radioimmunoassay has detected MIS in the follicular fluid of mature bovine ovaries (Vigier, B., et al., *Endocrinol.*, 114:1315-1320 (1984), in fluid from large and small follicles of new born ovaries (Necklaws, E., et al., *Endocrinol.*, 2:791-796 (1986), and in incubation media of bovine granulosa cells (Vigier, B., et al., supra (1984)).

MIS has been found to be cytotoxic to human ovarian cancer cells in vitro (Donahoe, P. K., et al., *Science*, 205:913-915 (1979)). It has also been found to be effective against this cancer in vivo (Donahoe, P. K., et al., U.S. Pat. No. 4,510,131).

The gene for MIS has been cloned and expressed in tissue culture cells; both the DNA and amino acid sequences are known (Cate, R. L. et al., *Cell* 45:685-698 (1986)).

II. Mammalian Embryology

The mammalian oocyte enters the first meiotic division during fetal life, but becomes arrested in late prophase (in the dictyate or diffuse diplotene stage of meiosis) before or just after birth (Beaumont, H. M., et al., *Proc. R. Soc. London* (Series Biological Sciences) 155:557-579 (1962). Resumption of meiosis normally does not occur until shortly before ovulation when a surge of gonadotropins prompts the resumption of meiotic maturation (Dekel, N., et al., *Proc. Natl. Acad. Sci. U.S.A.*, 75:4369-4373 (1978). Preovulatory resumption of meiosis is characterized by: (1) the breakdown of structures known as germinal vesicle (GV), (2) the expulsion of the first polar body and (3) progress to the metaphase of the second meiotic division (Tsafriri, A., et al., *J. Repro. Fertil.*, 64:541-551 (1982). In the rat, the period of MIS production by the ovary coincides with the period of oocyte meiotic arrest. The physiological mechanisms responsible for keeping the oocyte in the state of meiotic arrest are unknown but are not important to an understanding of the present invention. Such mechanisms are presumed to be regulated by the MIS of the present invention. It is, however, well-known that if rodent, bovine, or porcine oocytes are cultured in vitro, and subsequently isolated from follicles, they resume meiosis spontaneously (Edwards, R. G., *Nature*, 196:446-450 (1962); Foote, W. D., et al., *Anal. Biol. Animale Bioch. Biophys.* (Paris), 9:329-(1969)).

III. Inhibitors of Meiosis

Three different types of molecules have been reported to be involved in meiosis inhibition in mammalian oocytes: (1) a low-molecular weight protein fraction of follicular fluid or granulosa cells (termed "oocyte meiosis inhibitor"), (2) steroids, and (3) cAMP and other nucleotides (Downs, S. M., et al., *Proc. Natl. Acad. Sci. U.S.A.*, 82:454-458 (1985); McGaughey, R. W., *Endocrinol.*, 100:39-45 (1977); Dekel, N., et al., *Biol. Repro.*, 20:191-197 (1979); and Hubbard, C. J., et al., *Biol. Repro.*, 26:628-632 (1982)). Oocyte meiosis inhibitor is produced by granulosa cells, and is present in the Mullerian follicular fluid. Partial purification of this fluid has revealed the oocyte meiosis inhibitor to be a small polypeptide with a molecular weight of less than 6,000. Sato, E. et al., *Differentiation*, 26:59-62 (1984). This protein prevents the spontaneous resumption of meiosis in cultured cumulus cell-enclosed oocytes, but not in denuded oocytes. Hillensjo, T. et al., *Adv. Exper. Med. Biol.*, 147:175-188(1982). The protein's inhibitory effect can be overcome by Luteinizing Hormone (LH). The inhibitory effects can also be reversed by removing the factor from the culture medium (Sato, E. et al, supra).

Thus, in summary, the background art discloses that MIS, a high molecular weight glycoprotein, is produced by mammalian testes. MIS is capable of directing the regression of the Mullerian duct in a developing male embryo. In the absence of this substance, the Mullerian duct would continue its development into the female reproductive system.

Once formed in the developing embryo, the subsequent development of mammalian oocytes becomes arrested in the late prophase stage of meiosis. This inhibition of development is believed to be the result of interactions between the female reproductive system and either a low molecular weight oocyte meiosis inhibitor, steroids, or nucleotides, such as cAMP.

SUMMARY OF THE INVENTION

The present invention is based upon the discovery that Mullerian Inhibiting Substance has been found to inhibit oocyte meiosis. This inhibition prevents the formation of mature oocytes, and therefore results in a condition of infertility. Importantly, this inhibition is reversible through the administration of compounds such as Epidermal Growth Factor. Thus, the present invention relates to the use of MIS as a contraceptive agent. Applicant believes, but does not intend to be limited by this belief, that the contraceptive capability of MIS results from MIS's ability to interfere with oocyte maturation.

In detail, the invention provides a composition suitable for use as a contraceptive agent which comprises Mullerian Inhibiting Substance which is substantially free of natural contaminants.

Additionally, the invention relates to a method of contraception which comprises providing to a female an effective amount of the above composition.

The invention is also directed to a composition suitable for use as a fertility inducing agent which comprises an antibody capable of binding to Mullerian Inhibiting Substance the antibody being substantially free of natural contaminants.

The invention is further directed to a method of inducing fertility in a female which comprises providing to a female, an effective amount of the above antibody composition.

The invention is also directed toward a method for reversing the contraceptive activity of Mullerian Inhibiting Substance which comprises providing to a female recipient of Mullerian Inhibiting Substance an agent capable of reversing the contraceptive activity in an amount sufficient to achieve the reversal.

The invention additionally provides a method for controlling the fertility of a female which comprises:

(a) providing an initial amount of Mullerian Inhibiting Substance to a female sufficient to induce a condition of infertility in the female, (b) maintaining the condition of infertility for a desired period of time by providing an additional amount of Mullerian Inhibiting Substance to the female, and (c) when desired, providing an agent capable of reversing the condition of infertility induced by Mullerian Inhibiting Substance in an amount sufficient to induce a condition of fertility.

DESCRIPTION OF THE PREFERRED EMBODIMENTS

Figure 1:
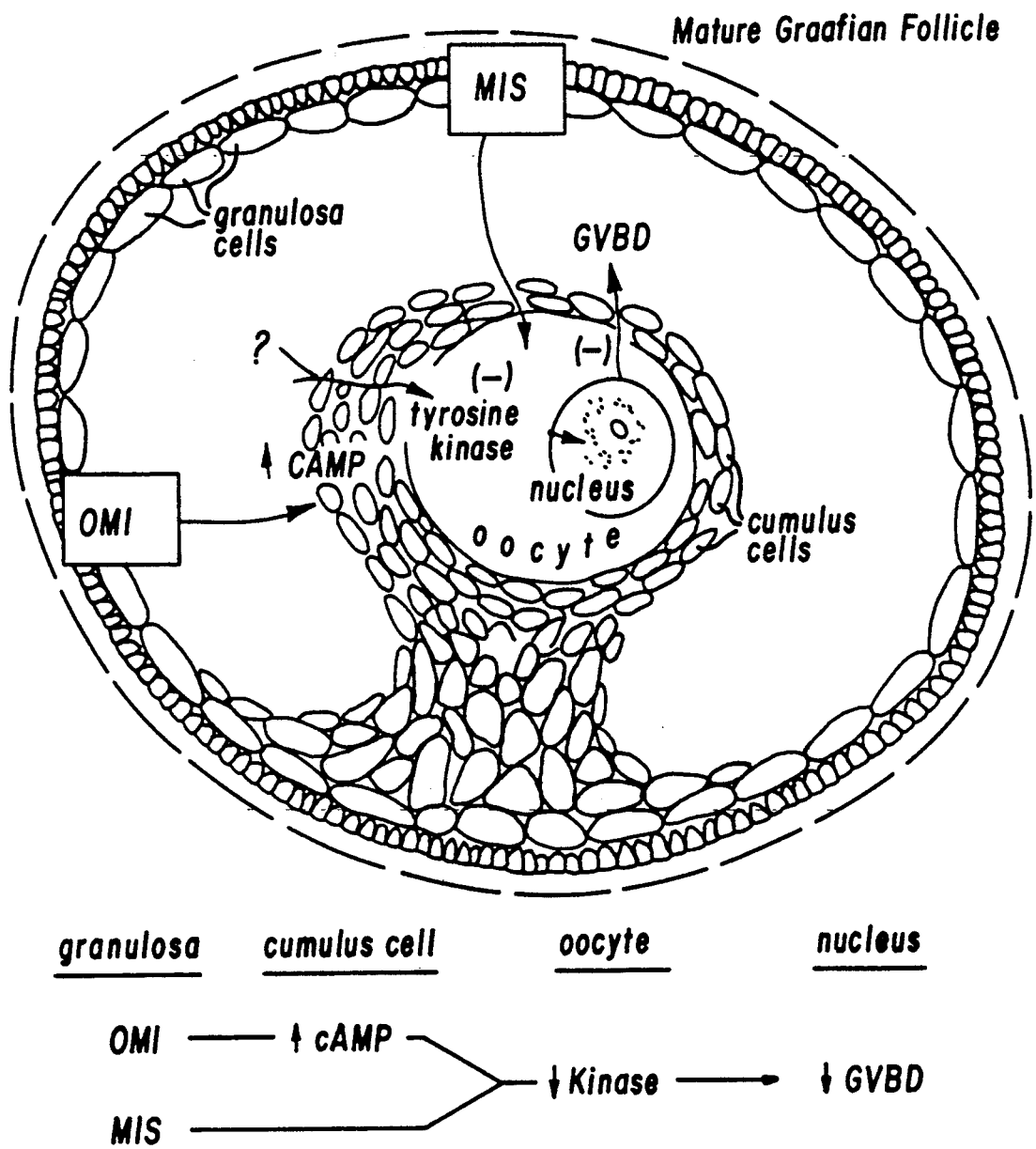
FIG. 1 is a drawing of a mature Graafian follicle showing the relative positions of the immature oocyte, cumulus cells, and the germinal vesicle structure.

Mullerian Inhibiting Substance may be obtained by a variety of different methods. The substance may be purified from testicular tissue according to the method of Donahoe, P. K., et al. (U.S. Pat. Nos. 4,510,131 and 4,404,188). Alternatively MIS may be purified from testicular tissue through the use of immuno-affinity chromatography as disclosed by Donahoe, P. K., et al. (U.S. Pat. No. 4,487,833). The material may also be obtained from recombinant DNA techniques (Cate, R. L. et al., *Cell,* 45: 685-698 (1986)).

The term "Mullerian Inhibiting Substance" (interchangeably referred to as "MIS") is intended to include compounds and materials which are structurally similar to MIS. Examples of such included substances and materials are salts, derivatives, and aglycone forms of MIS. Additionally, the present invention is intended to include mutant forms of MIS which have substantially the same biological activity as MIS. Examples of such mutant forms would be MIS molecules carrying a deletion, insertion, or alteration in amino acid sequence. MIS may be obtained from any mammalian source or, as indicated above, from non-mammalian sources through the use of recombinant DNA technology, or from the chemical synthesis of the MIS protein.

The term "peptide fragment" is meant to include both synthetic and naturally-occurring amino acid sequences derivable from the naturally occurring amino acid sequence of MIS.

A peptide is said to be "derivable from the naturally-occurring amino acid sequence of MIS" if it can be obtained by fragmenting the naturally-occurring chosen sequence of MIS, or if it can be synthesized based upon a knowledge of the sequence of the naturally occuring amino acid sequence or of the genetic material (DNA or RNA) which encodes this sequence.

A material is said to be "substantially free of natural contaminants" if it has been substantially purified from materials with which it is normally and naturally found but before purification. Examples of natural contaminants with which MIS might be associated are: other peptides, carbohydrates, glycosylated peptides, lipids, membrane, etc. A material is also said to be substantially free of natural contaminants if these contaminants are substantially absent from a sample of the material.

A gene is said to be a "recombinant"gene if it results from the application of Recombinant DNA Techniques. Examples of Recombinant DNA Techniques include cloning, mutagenesis, transformation, etc. Recombinant DNA Techniques are disclosed in Maniatis, T., et al., *Molecular Cloning: A Laboratory Manual,* Cold Spring Harbor, N.Y. (1982).

The invention further pertains to polypeptides that, in addition to the chosen sequence, may contain or lack one or more amino acids that may not be present in the naturally-occurring sequence, wherein such polypeptides are functionally similar to the chosen polypeptide. Such polypeptides for the present invention, are termed "functional derivatives," provided that they demonstrate activity which is substantially similar to that of MIS.

Included within the scope of the present invention are those peptide fragments in MIS which are capable of functioning as inhibitors of oocyte maturation. Included as well are the use of additional amino acid residues added to enhance coupling to carrier protein or amino acid residues added to enhance the inhibitory effect. As is known in the art, the amino acid residues of MIS may be in their protected or unprotected form, using appropriate amino or carboxyl protecting groups. The MIS may also be in the presence of cationic salt groups. Useful cations are alkali or alkaline earth metallic cations (i.e., Na, K, Li, ½Ca, ½Ba, etc.) or amine cations (i.e., tetraalkylammonium, trialkylammonium, where alkyl can be $C_1$-$C_{12}$).

The MIS composition may be in the form of the free amines (on the N-terminus), or acid-addition salts thereof. Common acid addition salts are hydrohalic acid salts, i.e., HBr, HI, or more preferably, HCl.

The MIS compositions of the present invention can be formulated according to known methods to prepare pharmaceutically useful compositions, whereby MIS or its functional derivatives are combined in admixture with a pharmaceutically acceptable carrier vehicle. Suitable vehicles and their formulation, inclusive of other human proteins, e.g. human serum albumin, are described for example in *Remington's Pharmaceutical Sciences* (16th Ed. A. Oslo Ed. Mack, Easton Pa. (1980)). In order to form a pharmaceutically acceptable composition suitable for effective administration, such compositions will contain an effective amount of the MIS, or its functional derivatives, together with a suitable amount of carrier vehicle.

An "effective amount" of MIS is one which is sufficient to achieve contraception in an ovulating human or animal. According to this invention contraception may be achieved by interfering with the natural development of arrested oocytes into mature oocytes. The effective amount may vary depending upon criteria such as the age, weight, physical condition, past medical history, and sensitivity of the recipient, but will preferably be between $10^{-7}$M to $10^{-2}$M.

Since the contraceptive activity of MIS is reversable, it is preferable to continuously provide an effective amount of MIS to a recipient in order to maintain a prolonged state of induced infertility. For example, monthly or bi-monthly administration can be used. Alternatively, slow release compositions can also be utilized. Factors which will effect the frequency of administration of MIS will include the pharmacokinetics of its persistance in the ovary, the potency of the preparation, etc.

Compositions containing MIS or its functional derivatives may be administered orally, intravenously, intramuscularly, subcutaneously, or locally.

For the purpose of parenteral administration, compositions containing MIS are dissolved in distilled water and the pH-value is adjusted to about 6 to 8. In order to facilitate the lyophilization process resulting in a suitable product, lactose could be added to the solution. The solution is then filter sterilized, introduced into vials, and lyophilized. The concentration of MIS in these compositions may vary from $10^{-7}$M to $10^{-2}$M.

Additional pharmaceutical methods may be employed to control the duration of action. Controlled release preparations may be achieved by the use of polymers to complex or adsorb MIS or its functional derivatives. The controlled delivery may be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release. Another possible method to control the duration of action by controlled release preparations is to incorporate MIS into particles of a polymeric material such as polyesters, polyamino acids, hydrogels, poly (lactic acid) or ethylene vinylacetate copolymers. Alternatively, instead of incorporating MIS into these polymeric particles, it is possible to entrap MIS in microcapsules prepared, for example, by coacervation techniques or by interfacial polymerization, for example, hydroxymethylcellulose or gelatin-microcapsules and poly (methylmethacrylate) microcapsules, respectively, or in colloidal drug delivery systems, for example, liposomes, albumin microspheres, microemulsions, nanoparticles, and nanocapsules or in macroemulsions. Such teachings are disclosed in *Remington's Pharmaceutical Sciences, supra* (1980).

The MIS of the present invention may be administered using either a "bolus" or a "sustained release medicament" composition. The term "bolus" is intended to refer to any administration which involves providing MIS in discreet and separable dosages. Pills, tablets, capsules, injections, etc., all constitute examples of administrations by bolus. The term "sustained release medicament" is intended to refer to any administration which involves providing MIS in a continuous and prolonged manner. Examples of sustained release medicaments include implants, infusions, time-release devices, etc.

The MIS of the present invention and its functional derivatives thereof, either alone or in pharmacologically acceptable compositions are useful as a contraceptive agent in ovulating humans or animals. The ability of MIS to interfere with normal oocyte maturation is believed, without being limiting of the invention, to be the cause of MIS's contraceptive efficacy.

One aspect of the present invention derives from the discovery that the contraceptive effect of MIS (i.e. the ability of MIS to inhibit oocyte maturation) may be reversed by compounds such as Epidermal Growth Factor (EGF). Both the effectiveness of MIS' contraceptive activity, and its susceptability to reversal by compounds such as EGF, increase with increasing MIS concentration. Epidermal Growth Factor is a peptide hormone which stimulates the growth and differentiating of epidermal tissues during embryogenesis (Carpenter, G., et al., *Exper. Cell. Res.* 164:1-10 (1986); Kris, R. M. et al., *Bio-Technol.* 3:135-140 (1985)). EGF may be purified from natural sources or may be obtained through application of recombinant DNA technology. The amount of EGF needed to reverse the contraceptive effects of MIS is generally determined through a consideration of the same factors as those considered in determining the dosage and mode administration of MIS. The amount of EGF needed to reverse the contraceptive effect will in general vary from about $10^{-7}$M to about $10^{-2}$M. EGF may be obtained from Collaborative Research, Lexington, Mass.

As would be obvious to one of ordinary skill in the art, the foregoing discussion on pharmaceutical compositions is equally applicable to the formulation of pharmaceutically appropriate formulations of epidermal growth factor or anti-MIS antisera.

The anti-MIS antisera or monoclonal antibody can be used to promote fertility in female patients if infertility is caused by abnormally high production of MIS. The antibody can be administered locally or by any other suitable technique. Dosages range from $10^{-7}$M to $10^{-2}$M.

Having now generally described this invention, the same will be better understood by reference to certain specific examples which are included herein for purposes of illustration only and are not intended to be limiting of the invention, unless specified.

EXAMPLE 1

Purification of Mullerian Inhibiting Substance

Mullerian Inhibiting Substance was purified according to the method of Budzik, G. P., et al., *Cell*, 21:909–915 (1980) and Budzik, G. P., et al., *Cell*, 34:307–314 (1983). Briefly, testes from calves less than two weeks of age were minced into 1 mm fragments in iced, serum-free Ham's F10 media (Budzik, G. P., et al (1980) supra) then incubated at 37° C. for 45 minutes with gentle agitation. The media was concentrated by ammonium sulfate precipitation, reequilibrated 250 mM NaCl, 10 mM sodium phosphate, 0.03% sodium azide, 1 mM EDTA, pH 8, and then applied to a diethylaminoethyl Bio-Gel A column. High biological activity was found in the unbound fraction. This fraction was then adjusted to pH 5 using dilute HCl, centrifuged at 40,000×g for 10 minutes to remove the precipitate, and the supernatant was then passed through a carboxymethyl Bio-Gel A column preequilibrated with 50 mM NaCl, 10 mM sodium phosphate, 0.03% sodium azide, 1 mM EDTA, pH 6. The unbound fraction, which again showed high biological activity, was concentrated 3 fold on an Amicon PM-30 ultrafilter and directly loaded into a wheatgerm lectin (WGL)-sepharose-6MB column (Budzik, G. P. et al. (1980) supra) equilibrated with 10 mM HEPES (pH 7), 150 mM NaCl, 1 mM EDTA, 5 mM 2-mercaptoethanol, 0.01% Nonidet P-40 (NP-40). After a buffer wash, the biologically active fraction was eluded with 100 mg/ml N-acetylglucosamine and loaded without further equilibration, onto an affinity column containing Matrex Gel Green $A^R$ (AMICON) (Budzik, G. P., et al. (1983), supra) previously equilibrated in 150 mM NaCl, 10 mM HEPES, 1 mM EDTA, 5 mM 2-mercaptoethanol, 0.01% NP-40, pH 8.0. After elution with this buffer alone and with 10 mM ATP, the bound fraction containing MIS biological activity was eluted with loading buffer containing 500 mM NaCl. This final fraction was concentrated 80 fold by vacuum dialysis against phosphate buffered saline containing 0.01% NP-40, and stored in 1 ml aliquots at −80° C. for subsequent use. Each vial contained 0.15 mg of protein per ml in phosphate buffered saline, (pH 7) and 0.01% NP-40). Dilutions of this material were made using Krebs-Ringer's bicarbonate (KRB) (Donahue, R. P., *J. Exper. Zool.* 169:237–250, (1968)) solution to produce MIS concentrations of $1.5\times10^{-2}$ to $1.5\times10^{-9}$ mg/ml.

EXAMPLE 2

Assay for Oocyte Maturation Inhibitory Activity

Ovaries of prepubertal Sprague-Dawley 25–27 day old rats (approximately 50 to 60 g body weight) or Swiss mice of approximately 15 to 20 g body weight were dissected immediately after sacrifice, and placed in the KRB solution described in Example 1. Dissected tissue was maintained on a warming plate at 35° C. The oocytes were visualized under a microscope and the cumulus enclosed oocyte was freed from the follicles by teasing with a sterile needle. In some cases, the adhereing cumulus oophorus cells were stripped from the oocytes by rapidly drawing the aggregated cells in and out of a pipet to yield a denuded oocyte. Fully grown oocytes containing an intact germinal vesicle with and without cumulus cells were used within 3 minutes after their isolation. Premature and small oocytes were discarded. 10–20 oocytes were pipetted into 0.2 ml of media under light paraffin oil, and cultured in an incubator for 1 to 24 hours immediately after recovery, at 37° C. The oocytes were continuously flushed with 95% air and 5% $CO_2$ saturated with water. FIG. 1 shows a diagramatic representation of a developing oocyte.

At each selected time, the oocytes were scored as immature (intact germinal vesicle with nucleolus) or as mature (if no germinal vesicle could be detected).

The percentage of oocytes in the two categories was calculated for each experimental treatment. To test differences between groups or statistical significance, the Chi Square test was used. A p-value less than 0.01 was considered significant.

EXAMPLE 3

Determination of the Time Sequence of Oocyte Maturation

Figure 2:
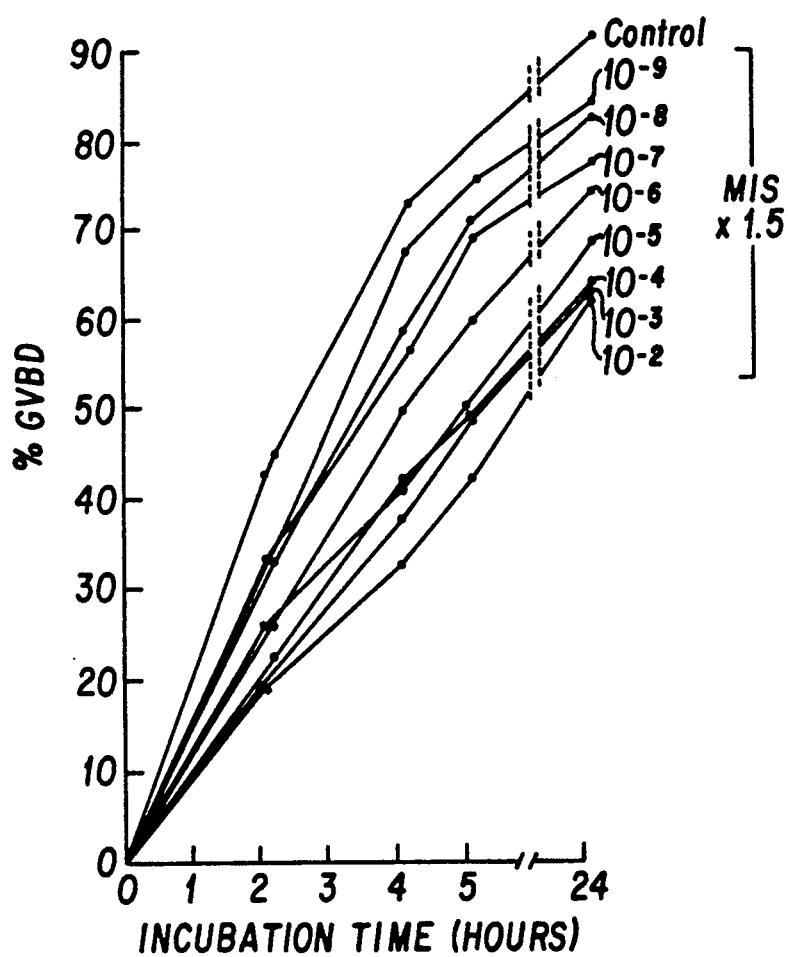
FIG. 2 shows the time sequence of oocyte maturation, as measured by germinal vesicle breakdown of denuded rat oocytes in the presence or absence of MIS.
Figure 3:
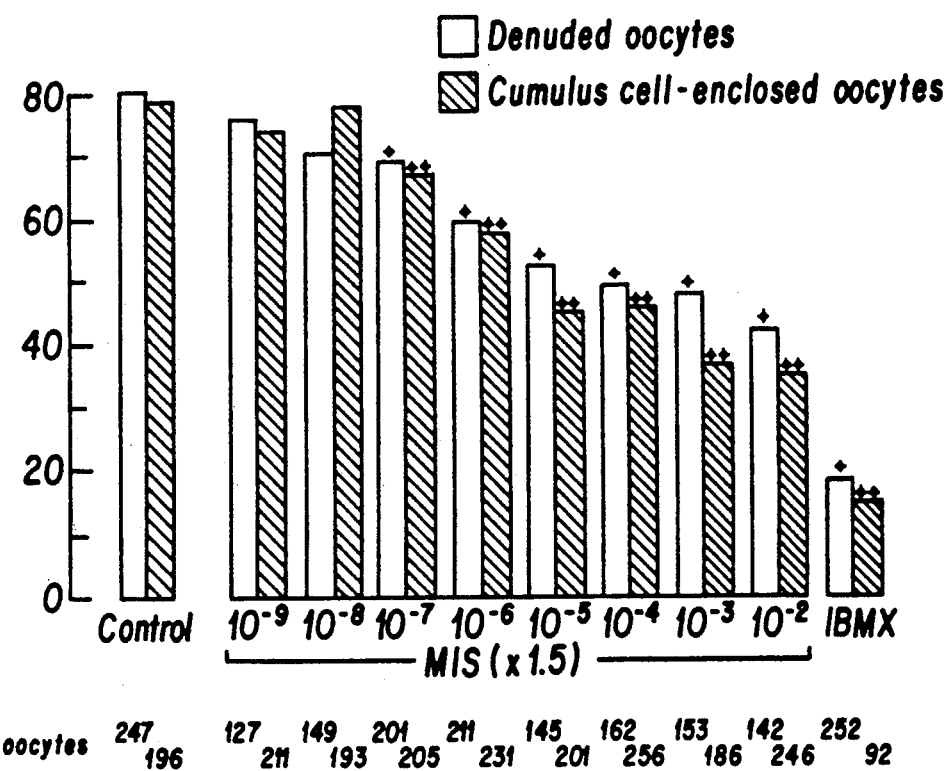
FIG. 3 shows the average percent of germinal vesicle breakdown which was found to occur in the presence or absence of MIS after an incubation period of 4-5 hours. Asterisks indicate that the significance of the data has a p-value of less than 0.01.

MIS was prepared as described in Example 1. The effect of MIS on the time sequence of oocyte maturation was determined through the use of the assay for oocyte maturation inhibitory activity described in Example 2. Thus, denuded rat oocytes were incubated with KRB media alone or with added MIS, and the time course and extent of germinal vesicle breakdown was determined. The percentage of spontaneous germinal vesicle breakdown of oocytes was calculated at incremental incubation times. After five hours of incubation and control media, spontaneous germinal vesicle breakdown occurred in more than 80% of denuded oocytes, indicating that a substantial number of oocytes were undergoing maturation. A significant and dose dependent inhibition of spontaneous germinal vesicle breakdown was observed in oocyte preparations which had been incubated in the presence of MIS containing fractions at concentrations of $1.5\times10^{-7}$ to $10^{-2}$ mg protein/ml. The results of this experiment are shown in FIG. 2. This experiment demonstrates that MIS is a potent inhibitor of oocyte maturation. As shown in FIG. 3, addition of the MIS containing fraction at these concentrations, but not $10^{-9}$ or $10^{-8}$ mg protein/ml caused significant and increasing inhibition of germinal vesicle breakdown of both denuded and cumulus cell-enclosed rat oocytes. At equimolar concentrations, there was no significant difference in the MIS-induced inhibition of germinal vesicle breakdown between denuded or cumulus cell-enclosed oocytes. The inhibiting effect of MIS on oocyte maturation, therefore, was found to be dose-dependent and cumulus cell-independent.

EXAMPLE 4

Reversibility of MIS Inhibition

Figure 4:
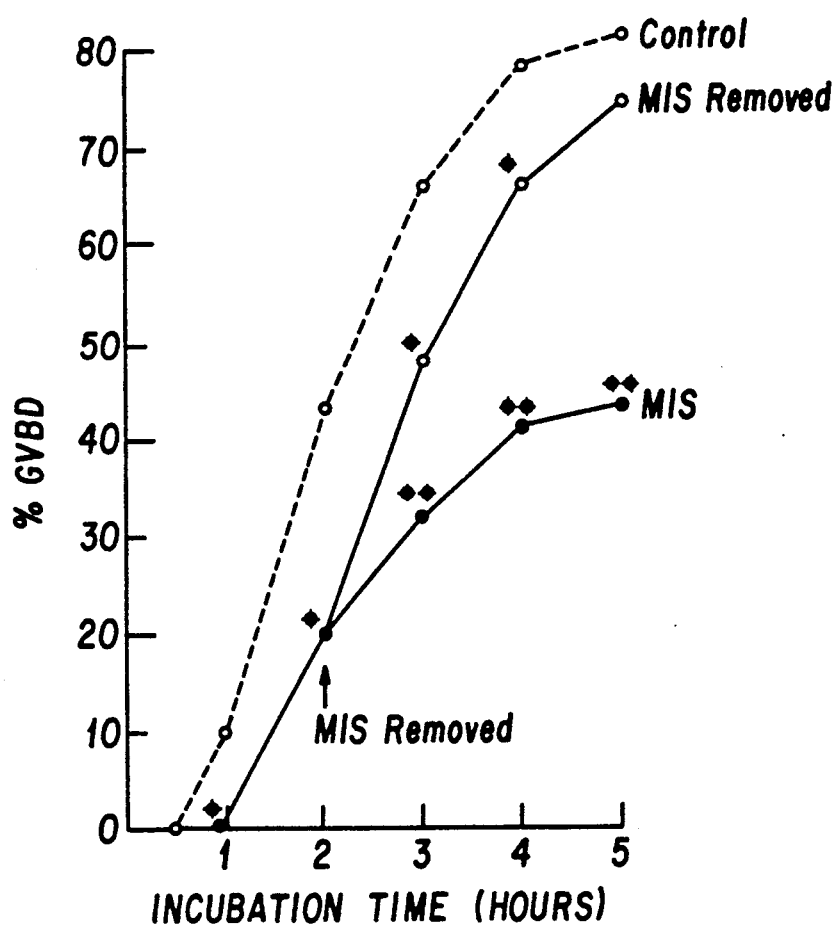
FIG. 4 shows the effect of the duration of MIS presence on the percentage of oocytes which undergo germinal vesicle breakdown. The reversibility of MIS activity is shown.

In order to determine whether MIS inhibition of oocyte maturation was reversible, a time course of oocyte maturation was determined. Thus, at hourly intervals denuded rat oocytes, as prepared in Example 2 were assayed for evidence of maturation in either the presence or absence of MIS. The results of this experiments are shown in FIG. 4. At one hour, 10% of denuded rat oocytes were found to have undergone spontaneous germinal vesicle breakdown in controlled media. This breakdown was found to increase in progressive increments until, at 5 hours, 81% of the oocytes initially present had undergone germinal vesicle breakdown. The presence of $1.5 \times 10^{-3}$ mg protein/ml MIS totally prevented the occurrence of germinal vesicle breakdown at 1 hour, and decreased germinal vesicle breakdown by approximately 50% (i.e., 43% of the oocytes had undergone germinal vesicle breakdown after 5 hours).

After 2 hours of MIS incubation, a portion of the oocyte sample was washed 3 times in KRB solution and transferred into a fresh KRB solution. 74% of oocytes so treated showed germinal vesicle breakdown after 5 hours, indicating that the MIS effect on denuded oocytes, was reversible.

This experiment further indicates that the contraceptive efficacy of MIS is dependent upon the continuous presence of an effective amount of MIS.

EXAMPLE 5

Effect of Dibutyryl Cyclic AMP on MIS Inhibition

Figure 5A:
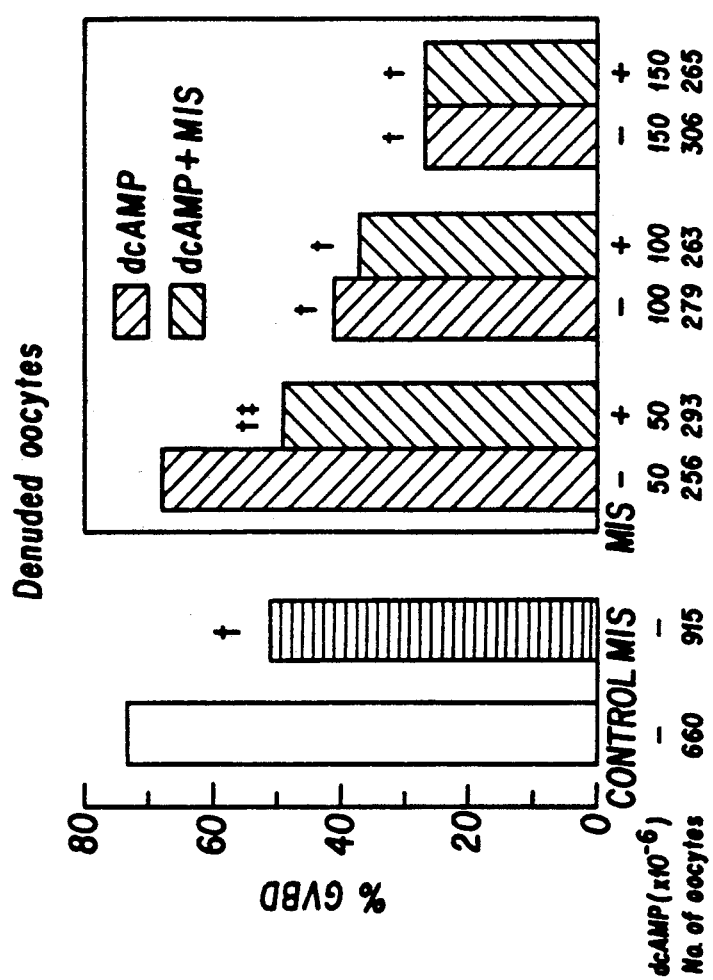
FIGS. 5A and 5B respectively show the effect of dibutyryl cyclic AMP and MIS on the percentage of denuded oocytes or cumulus cell-enclosed oocytes which undergo germinal vesicle breakdown.
Figure 5B:
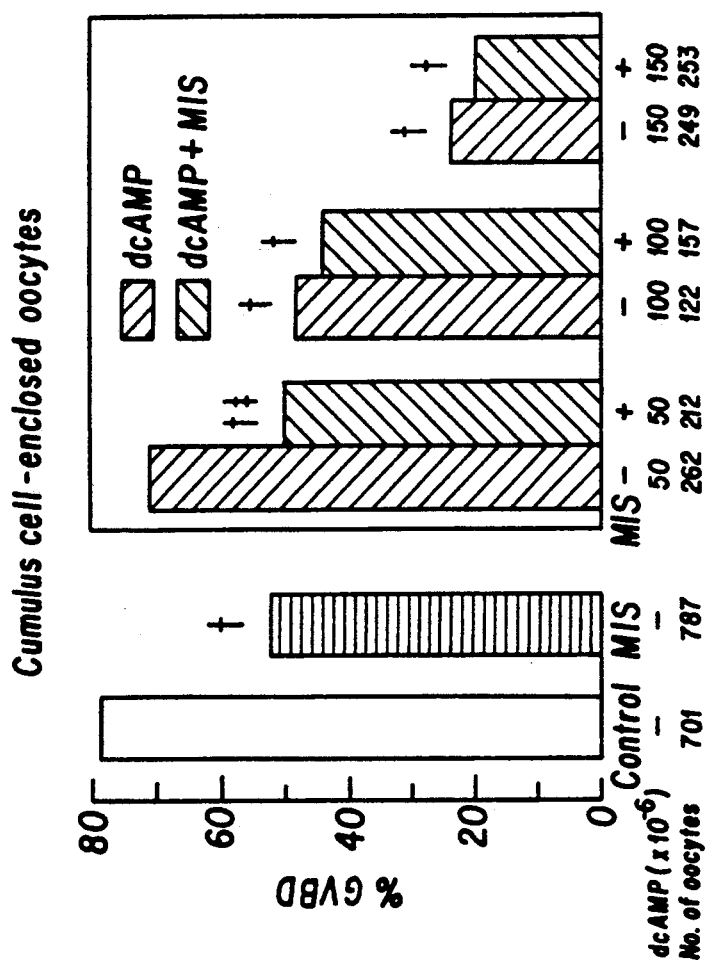

Rat oocytes were cultured for 5 hours hours in contolled media alone or with $1.5 \times 10^{-3}$ mg protein/ml MIS. Dibutyryl cyclic AMP (dbcAMP) at concentrations of 50, 100, or $150 \times 10^{-6}$ mM was incubated either alone or with $1.5 \times 10^{-3}$ mg protein/ml MIS. Adding $50 \times 10^{-6}$ M dbcAMP in KRB solution did not significantly alter the percentage oocytes undergoing germinal vesicle breakdown, nor influence the inhibitory effect of MIS (at the concentration of $1.5 \times 10^{-3}$ mg protein/ml). Adding $100 \times 10^{-6}$ M and $150 \times 10^{-6}$ M of dbcAMP in KRB solution significantly inhibited the spontaneous germinal vesicle breakdown, but did not enhance the inhibitory effect of $1.5 \times 10^{-3}$ mg protein/ml of MIS. These experiments were conducted on both denuded and cumulus cell-enclosed oocytes. The results of these experiments are shown in FIGS. 5A (denuded oocytes) and 5B (cumulus cell-enclosed oocytes).

This experiment shows that MIS does not act synergistically or antagonistically with dbcAMP to inhibit oocyte maturation. The experiment futher demonstrates that the MIS inhibitory effect was cumulus cell independent and cAMP-independent.

EXAMPLE 6

Figure 6:
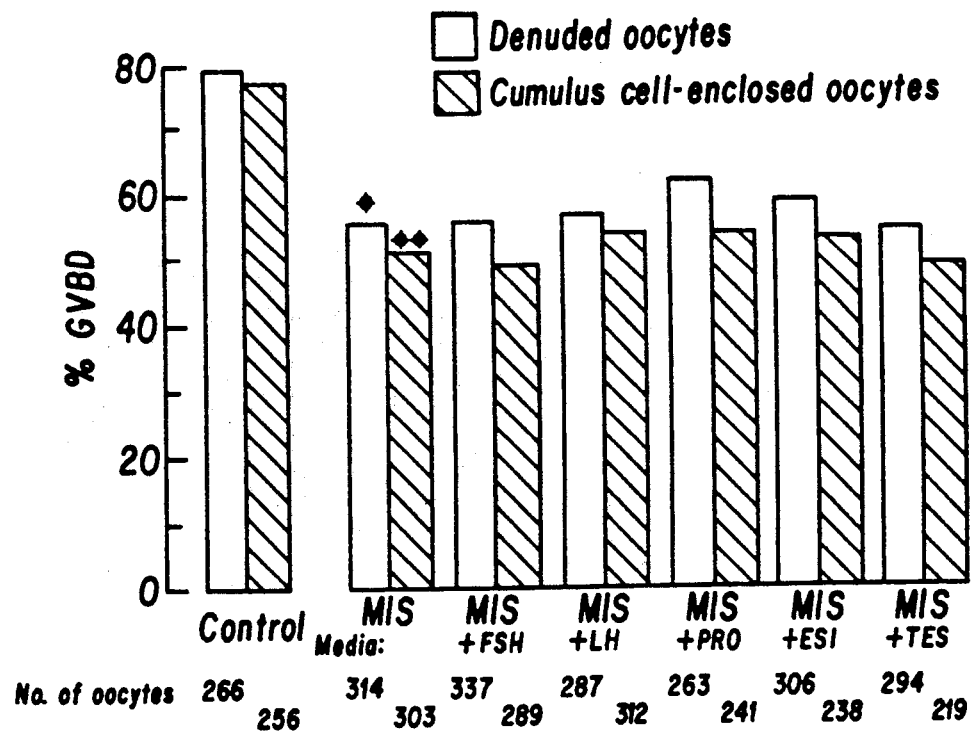
FIG. 6 shows the effect of reproductive hormones on MIS-induced inhibition of germinal vesicle breakdown in denuded and cumulus cell-enclosed oocytes.

Effect of Other Reproductive Hormones on MIS-Induced Inhibition of Oocyte Maturation The effect of reproductive hormones such as follicle stimulating hormone (FSH), luteinizing hormone (LH), progesterone, 17 beta-estradiol, and testosterone on MIS-induced inhibition was determined using denuded or cumulus cell-enclosed rat oocytes. To perform this determination, the assay for oocyte maturation inhibitory activity, described in Example 2 was preformed using denuded and cumulus cell-enclosed rat oocytes. MIS concentration was $1.5 \times 10^{-3}$ mg protein/ml. MIS-induced inhibition was assessed at varying hormone concentrations (0.1, 1.0, and 10 ug/ml FSH; 0.4, 4.0 and 40 ug/ml LH; 0.1, 1.0 and 10 ug/ml progesterone; 0.1, 1.0, and 10 ug/ml 17 beta-estardiol; and 0.1, 1.0, and 10 ug/ml testosterone). As shown in FIG. 6, these hormones failed to effect MIS-induced inhibition in either denuded or cumulus cell-enclosed oocytes. These results demonstrate that MIS-induced inhibition of oocyte maturation is independent of the presence or absence of other reproductive hormones.

EXAMPLE 7

Effect of Isobutylmethylxanthine on MIS-Induced Inhibition of Oocyte Maturation

Figure 7:
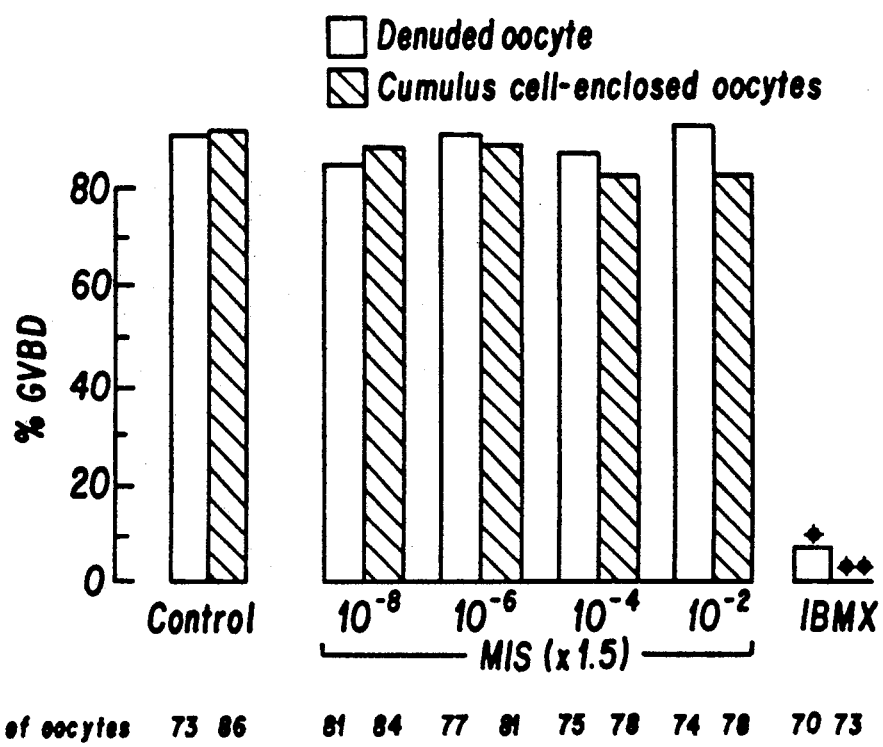
FIG. 7 shows the effect of MIS on germinal vesicle breakdown in denuded and cumulus cell-enclosed mouse oocytes.

Denuded and cumulus cell-enclosed mouse oocytes were cultured for 3 hours in control media alone or with $1.5 \times 10^{-2}$, $10^{-4}$, $10^{-6}$, or $10^{-8}$ mg protein/ml MIS, or $10^{-4}$ M isobutylmethylxanthine (IBMX). As shown in FIG. 7, addition of IBMX caused significant inhibition of spontaneous germinal vesicle in both the denuded and cumulus cell-enclosed oocytes. MIS was found to be incapable of inhibiting spontaneous germinal vesicle breakdown, indicating that bovine MIS did not have the inhibitory effect on mouse oocyte meiosis which had previously been observed in rat oocytes.

EXAMPLE 8

Effect of Anti-MIS Antisera on MIS Inhibition

Monoclonal antibodies capable of binding to purified MIS were prepared according to the method of Shima, H., et al. (Hybridoma, 3:201–214 (1984)). After initially screening the hybridoma cells for their ability to produce MIS-specific antibodies, positive hybridomas were further selected for their ability to inhibit MIS biological activity. Since MIS is an inhibitor of oocyte maturation, the administration of anti-MIS antisera (capable of inhibiting the biological activity MIS) is able to block and thereby reverse MIS inhibition. If female infertility is caused by an abnormal production of MIS, then the administration of an anti-MIS antibody such as those described above will be capable of restoring fertility.

EXAMPLE 9

Figure 8:
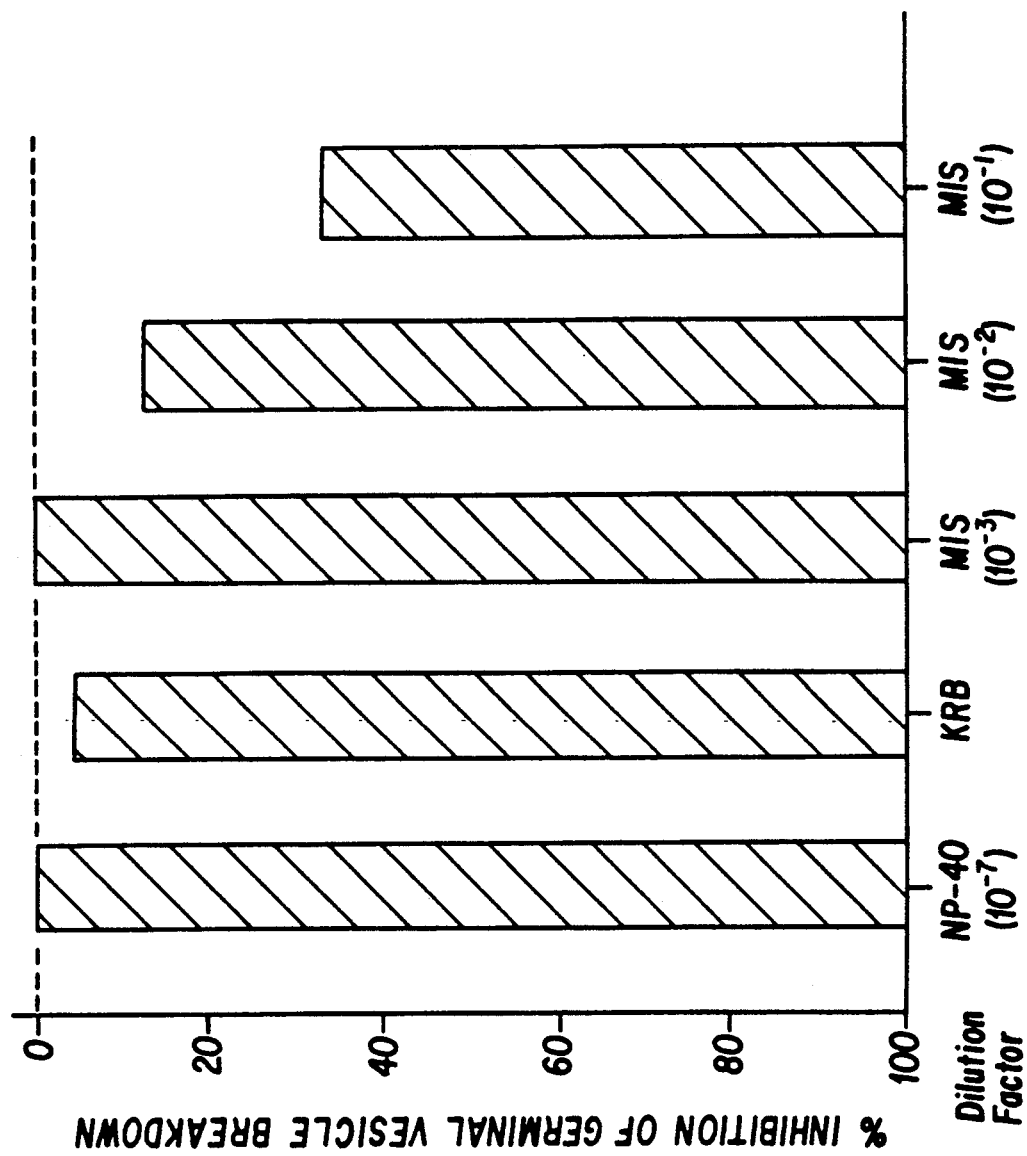
FIG. 8 shows the ability of recombinant Human MIS preparations to inhibit the breakdown of germinal vesicles.

Ability of Recombinant Human MIS Preparations to Inhibit Germinal Vesicle Breakdown The oocyte germinal vesicle breakdown assay of Example 2 was employed in order to test the ability of recombinant human MIS preparations to inhibit oocyte maturation. Recombinant human MIS was prepared by transfecting the MIS gene (Cate, R. L., et al., *Cell* 45:685–698 (1986)) into Chinese Hamster Ovary cells and growing the cells in a serum-free medium (adapted from the medium of Cate, R. L., et al., (1986)). The MIS was then purified by ion exchange and lectin affinity chromatography (Budzik, G.P., et al., *Cell* 21:909–921 (1980)) to obtain an MIS preparation containing possibly between 1–10% MIS, and more probably approximately 1% MIS. The results of this oocyte assay is shown in FIG. 8. As seen in this figure, neither the non-ionic detergent NP-40 (diluted $10^{-7}$ fold) nor Krebs-Ringer Buffer (KRB) were found to inhibit germinal vesicle breakdown. Serum-free recombinant human MIS was found to significantly inhibit germinal vesicle breakdown when diluted $10^{-2}$–$10^{-1}$ fold.

The ability of human recombinant MIS to inhibit germinal vesicle breakdown was found to require the presence of a non-ionic detergent (preferably NP-40) when diluted $10^{-6}$–$10^{-8}$ fold (most perferably at a dilution of $10^{-7}$ fold).

EXAMPLE 10

Ability of EGF to Reverse the Ability of MIS to Inihibit Oocyte Maturation

The oocyte germinal vesicle breakdown assay of Example 2 was employed in order to test the ability of EGF to reverse the contraceptive activity of MIS. Recombinant, human MIS, prepared according to the method of Example 9, was purified using dye affinity chromatography (Budzik, G. P., et al., *Cell* 34:307-314 (1983)). EGF was obtained from Collaborative Research, Lexington, Mass.

Figure 9:
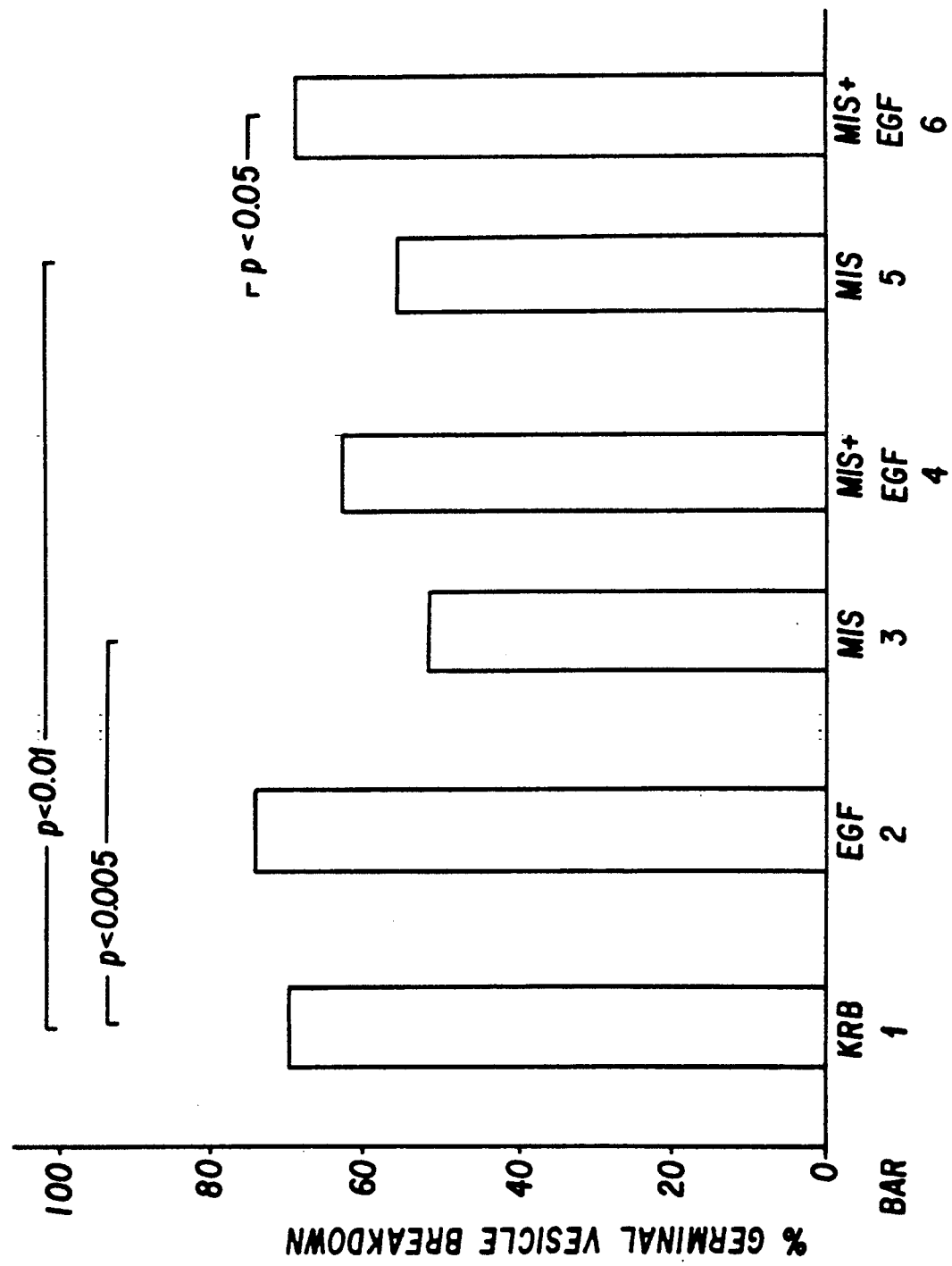
FIG. 9 shows the ability of epidermal growth factor to reverse the ability of MIS to inhibit germinal vesicle breakdown.

The results of this experiment are shown in FIG. 9. This figure shows that addition of KRB or EGF to the germinal vesicles was unable to inhibit the breakdown of the germinal vesicles (bars 1 and 2). Addition of MIS, purified using either DEAE/Green 3 or Fast Q ion exchange/Green 3 chromatography (bars 3 and 5, respectively), was found to inhibit germinal vesicle breakdown. The addition of EGF to a sample containing MIS resulted in a reversal of inhibition and a breakdown of germinal vesicles (bars 4 and 6, respectively). Thus, this example shows that the contraceptive effect of MIS can be reversed by EGF.

While the invention has been described in connection with specific embodiments thereof, it will be understood that it is capable of further modifications and this application is intended to cover any variations, uses, or adaptations of the invention, following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for reversing the contraceptive activity of Mullerian Inhibiting Substance which comprises providing to a female recipient of Mullerian Inhibiting Substance an Epidermal Growth Factor capable of reversing said contraceptive activity in an amount sufficient to achieve said reversal.

2. A method for controlling the fertility of a female which comprises:
   (a) providing an initial amount of Mullerian Inhibiting Substance to a female sufficient to induce a condition of infertility in said female,
   (b) maintaining said condition of infertility for a desired period of time by providing an additional amount of Mullerian Inhibiting Substance to said female, and
   (c) when desired, providing an Epidermal Growth Factor of reversing the condition of infertility induced by said Mullerian Inhibiting Substance in an amount sufficient to induce a condition of fertility.

3. The method of claim 2 wherein said additional amount of Mullerian Inhibiting substance is provided to said female as a bolus.

4. The method of claim 2 wherein said additional amount of Mullerian Inhibiting substance is provided as a sustained release medicament.

* * * * *